US00PP26694P3

(12) United States Plant Patent
Brown

(10) Patent No.: US PP26,694 P3
(45) Date of Patent: May 3, 2016

(54) ***OSTEOSPERMUM* PLANT NAMED 'KLEOE14215'**

(50) Latin Name: *Osteospermum ecklonis*
Varietal Denomination: KLEOE14215

(71) Applicant: Klemm+Sohn GmbH & Co. KG, Stuttgart (DE)

(72) Inventor: Graham Brown, Macquarie Fields (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 97 days.

(21) Appl. No.: 14/121,486

(22) Filed: Sep. 11, 2014

(65) Prior Publication Data

US 2016/0081252 P1 Mar. 17, 2016

(51) Int. Cl.
*A01H 5/02* (2006.01)

(52) U.S. Cl.
USPC ..... Plt./360

(58) Field of Classification Search
USPC ..... Plt./360
See application file for complete search history.

(56) References Cited

PUBLICATIONS

PLUTO Plant Variety Database country code CH. p. 1.*
PLUTO Plant Variety Database country code QZ. p. 1.*

* cited by examiner

*Primary Examiner* — Annette Para
(74) *Attorney, Agent, or Firm* — Barbara Campbell; Bethany R. Roahrig; Cochran Freund & Young, LLC

(57) ABSTRACT

A new *Osteospermum* plant particularly distinguished by medium sized flowers, white ray florets, violet-blue disc florets, and a horizontal spreading growth habit, is disclosed.

1 Drawing Sheet

Genus and species: *Osteospermum ecklonis.*
Variety denomination: 'KLEOE14215'.

BACKGROUND OF THE NEW PLANT

The present invention comprises a new and distinct variety of *Osteospermum*, botanically known as *Osteospermum ecklonis*, and hereinafter referred to by the variety name 'KLEOE14215'. 'KLEOE14215' originated from a cross-pollination conducted in March 2007 in Macquarie Fields, Australia between the proprietary female *Osteospermum* variety 'x07.1.1' (unpatented), and the proprietary male *Osteospermum* variety 'x07.1.5' (unpatented).

The seeds from the cross were sown and plants were grown in a greenhouse for evaluation, where an individual plant designated 'KLEOE14215' was selected from the group of plants in July 2008 in Cobbity, NSW, Australia. In September 2008 in Cobbity, NSW, Australia, 'KLEOE14215' was first vegetatively propagated by vegetative cuttings. 'KLEOE14215' was found to reproduce true to type in successive generations of asexual propagation via vegetative cuttings.

CROSS REFERENCE TO RELATED APPLICATIONS

Plant Breeder's Rights for 'KLEOE14215' were applied for in Europe with the Community Plant Variety Office on Nov. 21, 2013, Application No. 2013/2954; in Switzerland on Dec. 9, 2013, Application No. 13-2921; and in Norway on Jan. 17, 2014, Application No. 1323. 'KLEOE14215' has not been made publicly available or sold more than one year prior to the filing date of this application.

SUMMARY

The following are the most outstanding and distinguishing characteristics of this new variety when grown under normal horticultural practices in Stuttgart, Germany.

1. Medium sized flowers;
2. White ray florets;
3. Violet-blue disc florets; and
4. A horizontal spreading growth habit.

DESCRIPTION OF THE PHOTOGRAPH

This new *Osteospermum* plant is illustrated by the accompanying photograph which shows the plant's overall plant habit including form, foliage, and flowers. The photograph is of a four-month-old plant grown in a greenhouse in Stuttgart, Germany in September 2012. The colors shown are as true as can be reasonably obtained by conventional photographic procedures.

DESCRIPTION OF THE NEW VARIETY

The following detailed descriptions set forth the distinctive characteristics of 'KLEOE14215'. The data which define these characteristics were collected from asexual reproductions carried out in Stuttgart, Germany. Data was collected on six-month-old plant grown in a greenhouse in Stuttgart, Germany in May 2014. Color references are to The R.H.S. Colour Chart of The Royal Horticultural Society of London (R.H.S.), 5$^{th}$ edition (2007).

Classification:

*Family.*—Asteraceae.
*Botanical.—Osteospermum ecklonis.*
*Common.—Osteospermum*
*Designation*—'KLEOE14215'. .

Parentage:
*Female parent.*—The proprietary female *Osteospermum* variety 'x07.1.1' (unpatented).
*Male parent.*—The proprietary male *Osteospermum* variety 'x07.1.5' (unpatented).
Plant:
*Form and habit.*—Herbaceous perennial but usually cultivated as an annual.
*Growth habit.*—Horizontal spreading.
*Branching habit.*—Freely branching.
*Height (from top of soil, including inflorescence).*—About 10.0 cm.
*Width (including inflorescences).*—About 50.0 cm to 60.0 cm.
*Propagation.*—Vegetative cuttings.
*Time to produce a finished flowering plant.*—14 weeks (in the spring).
*Time to initiate and develop roots.*—3 weeks (in the spring).
*Root description.*—Freely rooting.
Leaves:
*Arrangement.*—Alternate.
*Shape.*—Dentiform.
*Apex.*—Obtuse to acute.
*Base.*—Acute.
*Margin.*—Entire to serrate.
*Immature color.*—Upper surface: RHS 143A. Lower surface: RHS 143B.
*Mature color.*—Upper surface: RHS 137A. Lower surface: RHS 137C.
*Length.*—Up to 5.0 cm.
*Width.*—Up to 3.0 cm.
*Texture and appearance (upper and lower surfaces).*—Leathery, glabrous.
*Petioles.*—Absent.
*Venation pattern.*—Pinnate.
*Venation color (both upper and lower surfaces).*—RHS 138B.
Stems:
*Total number of branches per plant (calculated at the base of the plant).*—About 3 to 5.
*Length.*—Up to 20.0 cm.
*Diameter.*—0.6 cm.
*Internode length.*—2.0 cm to 3.0 cm.
*Color.*—RHS 144C.
*Texture.*—Smooth, glabrous.
*Anthocyanin.*—Absent.
Flower buds:
*Shape.*—Ovate.
*Length.*—About 1.0 cm.
*Diameter.*—About 0.7 cm.
*Color (at tight bud just before the ray florets unfold).*—RHS 143A.
Inflorescence:
*Type.*—Single.
*Blooming habit.*—Spring to autumn.
*Quantity of inflorescences per plant.*—15 to 20.
*Lastingness of the inflorescences on the plant.*—About 2 weeks.
*Fragrance.*—Faint.
*Inflorescence diameter.*—About 7.0 cm.
*Inflorescence depth.*—About 1.0 cm.
*Disc diameter.*—About 1.2 cm.
Disc floret:
*Quantity per inflorescence.*—25 to 30.
*Shape.*—Tubular lanceolate.
*Tube color.*—Closed: RHS 101B (outer surface at an immature state). Mature: RHS 96B (both inner and outer surface).
*Length.*—About 0.5 cm.
*Diameter (at apex).*—About 0.1 cm.
*Apex.*—Obtuse.
*Apex color.*—RHS 98A.
*Base.*—Acute.
*Base color.*—RHS 155C.
*Margin.*—Entire.
Ray floret:
*Quantity per inflorescence.*—About 14.
*Shape.*—Oblanceolate.
*Color.*—Upper surface: RHS NN155D. Lower surface: RHS 76B with RHS 97A stripes.
*Length.*—About 3.5 cm.
*Width.*—About 0.9 cm.
*Apex.*—Obtuse to acute.
*Base.*—Acute.
*Margin.*—Entire.
*Texture.*—Upper surface: Smooth. Lower surface: Smooth, shiny.
Peduncle:
*Length.*—3.0 to 4.0 cm.
*Diameter.*—0.2 cm.
*Texture.*—Rough, glabrous.
*Color.*—RHS 143B.
Phyllaries:
*Texture.*—Rough, glabrous.
*Color.*—RHS 143A.
*Arrangement.*—Single.
*Observed quantity per plant.*—About 14.
*Shape.*—Lanceolate.
*Color.*—Upper surface: RHS 143A. Lower surface: RHS 143B.
*Length.*—About 1.0 cm.
*Width.*—About 0.15 cm.
*Apex.*—Acute.
*Base.*—Acute.
*Margin.*—Entire.
*Texture.*—Upper surface: Rough. Lower surface: Smooth.
Reproductive organs:
*Androecium.*—Location: On the disc floret. Stamens: Quantity: Numerous. Shape: Filamentous. Filament length: About 0.5 cm. Filament diameter: Less than 0.05 cm. Anther: Shape: Lanceolate. Color: RHS N186B. Length: About 0.2 cm. Diameter: Less than 0.05 cm. Pollen: Color: RHS 17B. Amount: Abundant.
*Gynoecium.*—Location: On the base of the ray florets. Pistils: Number: About 14. Length: About 0.5 cm. Diameter: Less than 0.05 cm. Stigma: Color: RHS 79A. Shape: Tapering filamentous. Length: 0.2 cm. Diameter: Less than 0.05 cm. Style: Color: RHS 83C. Length: 0.2 cm. Diameter: Less than 0.05 cm.
Fruit and seed set: None observed.
Disease and pest/insect resistance: No disease and pest/insect resistance observed.

COMPARISON WITH PARENTAL LINES AND KNOWN VARIETY

'KLEOE14215' is a distinct variety of *Osteospermum* and is distinguished from its parents as described in Table 1.

TABLE 1

| Comparison with Parental Lines | | | |
|---|---|---|---|
| Characteristic | 'KLEOE14215' | Female Parent 'x07.1.1' | Male Parent 'x07.1.5' |
| Habit | Horizontal spreading | Mounding | Mounding |
| Flower size | Medium | Large | Large |
| Diameter of the plant | 50.0 cm to 60.0 cm | 100.0 cm | 100.0 cm |

'KLEOE14215' is most similar to the commercial *Osteospermum* variety 'KLEOE03106' (unpatented), also commercially known as FlowerPower™ 'White'. Differences between the varieties are described in Table 2.

TABLE 2

| Comparison with Similar Variety | | |
|---|---|---|
| Characteristic | 'KLEOE14215' | 'KLEOE03106' |
| Growth habit | Horizontal spreading | Upright |

I claim:

1. A new and distinct variety of *Osteospermum* plant designated 'KLEOE14215' as shown and described herein.

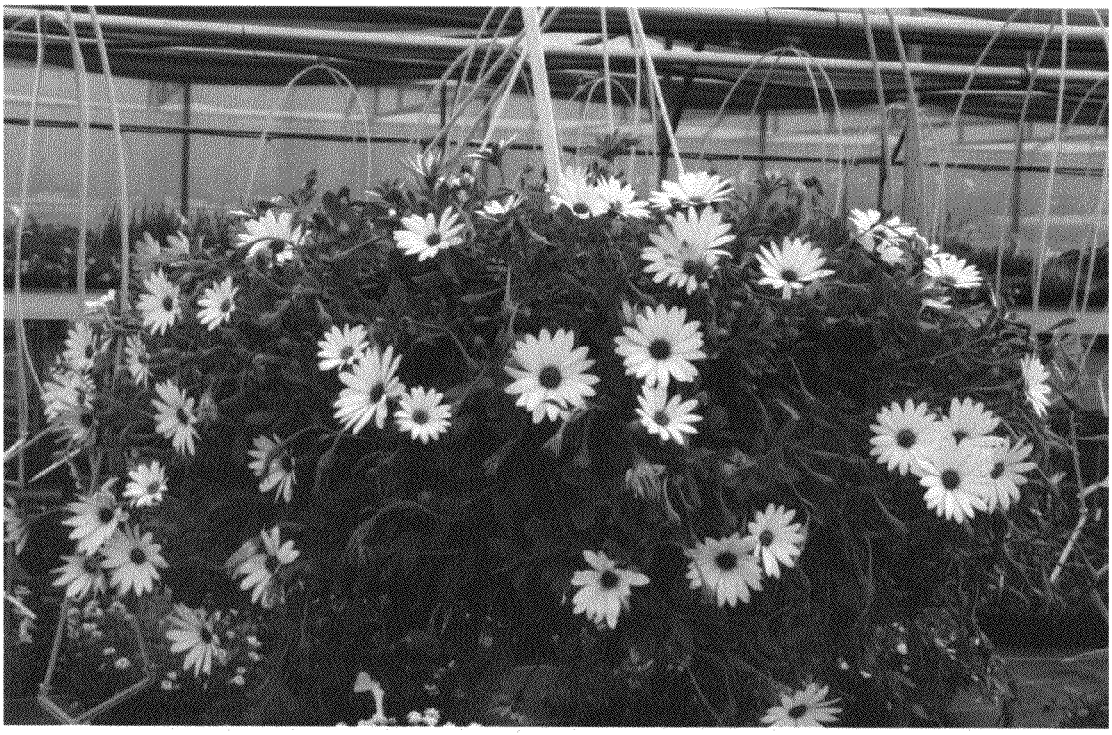

* * * * *